United States Patent [19]
Ito

[11] Patent Number: 5,837,717
[45] Date of Patent: Nov. 17, 1998

[54] HYDROXAMIC ACID ANESTHETIC COMPOUNDS

[75] Inventor: Fumitaka Ito, Aichi-ken, Japan

[73] Assignee: Pfizer Inc., New York, N.Y.

[21] Appl. No.: 790,246

[22] Filed: Jan. 28, 1997

[30] Foreign Application Priority Data

Feb. 7, 1996 [WO] WIPO ............ PCT/IB96/00099

[51] Int. Cl.[6] ............... A61K 31/445; A61K 31/44; C07D 401/12; C07C 291/02

[52] U.S. Cl. ............ 514/326; 514/212; 514/331; 514/357; 514/428; 514/644; 540/610; 546/233; 546/336; 548/587; 548/950; 564/299

[58] Field of Search ............ 540/610; 546/233, 546/336, 587, 950; 564/299; 514/212, 331, 357, 428, 644, 326

[56] References Cited

U.S. PATENT DOCUMENTS

| | | | |
|---|---|---|---|
| 5,128,364 | 7/1992 | Girard | 514/411 |
| 5,132,319 | 7/1992 | Girard | 514/415 |
| 5,232,978 | 8/1993 | Gottschlich | 514/422 |
| 5,292,884 | 3/1994 | Honn | 546/216 |

FOREIGN PATENT DOCUMENTS

| | | |
|---|---|---|
| 0254545 | 1/1988 | European Pat. Off. . |
| 0483580 | 5/1992 | European Pat. Off. . |

OTHER PUBLICATIONS

O'Brien "Receptor binding in drug research" Marcel Dekker Inc. pp. 185–197, 1987.

*Primary Examiner*—Ceila Chang
*Attorney, Agent, or Firm*—Peter C. Richardson; Paul H. Ginsburg

[57] ABSTRACT

A compound of the following formula:

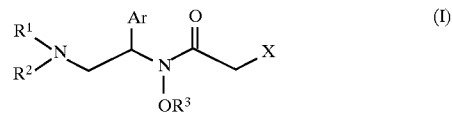

and its pharmaceutically acceptable salt thereof, wherein $R^1$ and $R^2$ are independently hydrogen, $C_{1-4}$ alkyl, $C_{3-7}$ cycloalkyl, $C_{2-4}$ alkenyl, $C_{1-4}$ alkoxy, $C_{1-4}$ alkylthio, phenyl or phenyl-$C_{1-4}$alkyl; or $R^1$ and $R^2$ are taken together with the nitrogen to which they are attached and form optionally substituted, saturated or unsaturated 3-, 4-, 5-, 6- or 7-membered heterocyclic containing one to two heteroatoms, provided that the heterocyclic is not pyrrolidinyl;

$R^3$ is hydrogen, $C_{1-4}$ alkyl or a hydroxy protecting group;

Ar is phenyl optionally substituted with one or more substituents selected from halo, hydroxy, $C_{1-4}$ alkyl, $C_{1-4}$ alkoxy, $C_{1-4}$ alkoxy-$C_{1-4}$ alkyloxy, $CF_3$ and carboxy-$C_{1-4}$ alkyloxy; and X is phenyl, naphthyl, biphenyl, indanyl, benzofuranyl, benzothiophenyl, 1-tetralone-6-yl, $C_{1-4}$ alkylenedioxy, pyridyl, furyl or thienyl, these groups being optionally substituted with up to three substituents. These compounds and pharmaceutical compositions containing them are useful as analgesic, antiinflammatory, diuretic, antitussive, anesthetic or neuroprotective agents, or an agent for treatment of functional bowel disease such as abdominal pain, for the treatment of a mammalian subject, especially a human subject.

9 Claims, No Drawings

HYDROXAMIC ACID ANESTHETIC COMPOUNDS

TECHNICAL FIELD

This invention relates to novel hydroxamic acid derivatives and their pharmaceutically acceptable salts, and to pharmaceutical compositions containing them. These compounds and compositions are useful as analgesic, antiinflammatory, diuretic, antitussive, anesthetic or neuroprotective agents, or an agent for treatment of functional bowel disease such as abdominal pain, for the treatment of a mammalian subject, especially a human subject.

BACKGROUND ART

Opioid analgesics such as morphine are therapeutically useful, but their usage is strictly limited because of their side effects such as drug dependency. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as a, $\mu$, δ, κ at a peripheral nerve in a variety of species, including human, has made a beginning towards creating new analgesics. As it is thought that opioid analgesics such as morphine act as a $\mu$-receptor agonist, separating the action based on a κ-receptor agonist from the action based on $\mu$-receptor agonist has been investigated.

Recently κ-selective agonists have been reported from the above viewpoint for example, EMD-60400: A. Barber et al., Naunyn-Schmled. Arch. Pharmacol., 345 (Suppl.): Abst 456. Some of them actually have been studied in clinical trials (Med. Res. Rev., 12, 525 (1992)). Examples of κ-selective agonists have been disclosed in European Patent Nos. EP 0 254545 B1 and EP 0 483580 A2.

BRIEF DISCLOSURE OF THE INVENTION

The present invention provides a compound of the following formula:

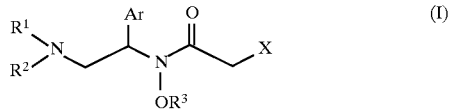

and its pharmaceutically acceptable salt thereof, wherein $R^1$ and $R^2$ are independently hydrogen, $C_{1-4}$ alkyl, $C_{3-7}$ cycloalkyl, $C_{2-4}$ alkenyl, $C_{1-4}$ alkoxy, $C_{1-4}$ alkylthio, phenyl or phenyl-$C_{1-4}$ alkyl; or $R^1$ and $R^2$ are taken together with the nitrogen to which they are attached and form optionally substituted, saturated or unsaturated 3-, 4-, 5-, 6- or 7-membered heterocyclic cantaining one to two heteroatoms, provided that the heterocyclic is not pyrrolidinyl;

$R^3$ is hydrogen, $C_{1-4}$ alkyl or a hydroxy protecting group;

Ar is phenyl optionally substituted with one or more substituents (preferably up to three) selected from halo, hydroxy, $C_{1-4}$ alkyl, $C_{1-4}$ alkoxy, $C_{1-4}$ alkoxy-$C_{1-4}$ alkyloxy, $CF_3$ and carboxy-$C_{1-4}$ alkyloxy; and X is phenyl, naphthyl, biphenyl, indanyl, benzofuranyl, benzothiophenyl, 1-tetralone-6-yl, $C_{1-4}$ alkylenedioxy, pyridyl, furyl or thienyl, these groups being optionally substituted with up to three substituents selected from halo, $C_{1-4}$ alkyl, $C_{1-4}$ alkoxy, hydroxy, $NO_2$, $CF_3$ and $SO_2CH_3$.

These compounds and pharmaceutical compositions containing them are useful as analgesic, antiinflammatory, diuretic, antitussive, anesthetic or neuroprotective agents, or an agent for treatment of functional bowel disease such as abdominal pain, for the treatment of a mammalian subject, especially a human subject.

DETAILED DISCLOSURE OF THE INVENTION

In this specification, the term "heterocyclic" means cyclic rings or ring systems containing at least one nitrogen atom and 2 to 16 carbon atoms, and additionally containing the other hetero atom such as O or S, which may include mono-, bi- or tri-cyclic systems, preferably mono cyclic systems. Representative examples includes, but are not limited to, piperidino, pyrrolino, 1, 2, 3, 6-tetrahydropyridino, azethidynyl, hexametheneimino, morpholino, thiamorpholino, pyrazolino, pyrazolidino or pipeiazinyl, preferbly piperidino, pyrrolino, 1, 2, 3, 6-tetrahydropyridino, azethidynyl and 2-hexametheneimino. The heterocyclic may optionally be substituted with $C_{1-6}$ alkyl, $C_{1-6}$ alkoxy, $C_{2-6}$ alkenyl, halo (i.e., fluoro, chloro, bromo or iodo), benzyl, substituted benzyl, hydroxy, carboxy, cyano, nitro, di $C_{1-6}$ alkylamino, amino, $C_{1-6}$ alkylsufonylamino, mercapt, $C_{1-6}$ alkylthio, $C_{1-6}$ alkylsulfinyl, $C_{1-6}$ alkylsulfonyl, phenyl, phenoxy and the like.

A preferred group of compounds of this invention includes the compound of the formula (I) wherein $R^1$ and $R^2$ taken together forms a 5- or 6-membered cyclic amino group optionally substituted with one to three substituents selected from hydroxy, halo, $C_{1-4}$ alkyl and —OY wherein Y is a hydroxy protecting group.

Preferably Ar is phenyl.

Among these preferabley X is phenyl substituted with up to three substituents selected from chloro, methyl and $CF_3$, preferably 3,4-dichlorophenyl; and $R^3$ is hydrogen.

Preferred individual compounds of the invention are:
2-(3,4-dichlorophenyl)-N-(1-(S)-phenyl-2-piperidinoethyl)-N-tetrahydropyranyloxyacetamide;
2-(3,4-dichlorophenyl)-N-hydroxy-N-(1-(S)-phenyl-2-piperidinoethyl)acetamide;
2-(3,4-dichlorophenyl)-N-hydroxy-N-[1-(S)phenyl-2-(3-pyrrolinoethyl)]acetamide;
2-(3,4-dichlorophenyl)-N-[1-(S)-phenyl-2-(1,2,3,6-tetrahydropyridin-1-yl)ethyl]-N-tetrahydropyranyloxyacetamide;
2-(3,4-dichlorophenyl)-N-hydroxy-N-[1-(S)-phenyl-2-(1,2,3,6-tetrahydropyridin-1-yl)ethyl]acetamide;
2-(3,4-dichlorophenyl)-N-(2-N,N-dimethylamino-1-(S)-phenylethyl)-N-hydroxyacetamide;
N-(2-azetidinyl-1-(S)-phenylethyl)-N-hydroxy-2-(3,4-dichlorophenyl)acetamide;
2-(3,4-dichlorophenyl)-N-(2-hexamethyleneimino-1-(S)-phenylethyl)-N-hydroxyacetamide;
2-(2,3-dichlorophenyl)-N-hydroxy-N-[1-(S)-phenyl-2-(1,2,3,6-tetrahydropyridin-1-yl)ethyl]acetamide; and
N-hydroxy-N-[1-(S)-phenyl-2-(1,2,3,6-tetrahydropyridin-1-yl)ethyl]-2-(2,3,6-trichlorophenyl)acetamide.

Most preferred individual compounds of the invention are:
2-(3,4-dichlorophenyl)-N-hydroxy-N-(1-(S)-phenyl-2-piperidinoethyl)acetamide;
2-(3,4-dichlorophenyl)-N-hydroxy-N-[1-(S)-phenyl-2-(3-pyrrolinoethyl)]acetamide; and
2-(3,4-dichlorophenyl)-N-hydroxy-N-[1-(S)-phenyl-2-(1,2,3,6-tetrahydropyridin-1-yl)ethyl]acetamide.

The hydroxyamic compounds of present invention of the formula (I) exhibit significant agonist activity toward opioid κ receptor and thus useful as analgesic, antiinflammatory, diuretic, antitussive, anesthetic or neuroprotective agents, or an agent for treatment of functional bowel disease such as abdominal pain, for the treatment of a mammalian subject, especially a human subject.

Accordingly, the present invention also provides a pharmaceutical composition useful as an analgesic, antiinflammatory, antitussive, diuretic, anesthetic or neuroprotective agent, or an agent for treatment of functional bowel disease, which comprises a compound of formula (I), and a pharmaceutically inert carrier.

The present invention also provides a method for the treatment of a medical condition for which agonist activity toward opioid κ receptor is needed, in a mammalian subject, which comprises administering to said subject a therapeutically effective amount of a compound of formula (I).

General Synthesis

The κ agonists of formula (I) of this invention can be prepared by a number of methods. For example, they can be readily prepared according to the procedure shown in Scheme I below.

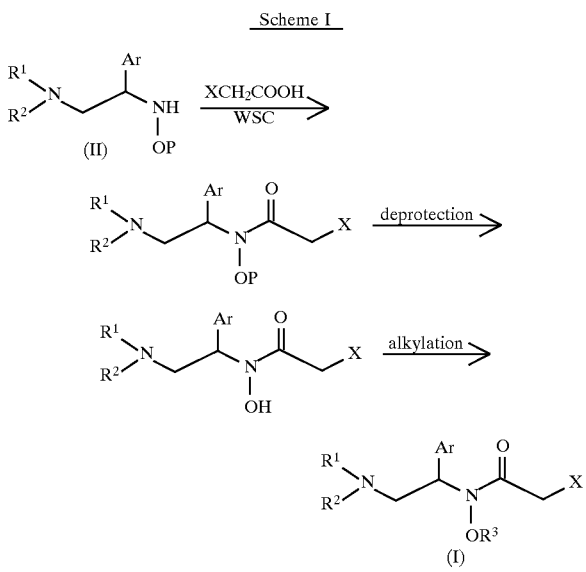

The κ agonist compounds of formula (I) can be prepared by reaction of a compound of the formula (II) with a carboxylic acid of the formula $XCH_2COOH$, followed by removal of the protecting group P. This is a conventional acylation reaction, which can be carried out using standard methods, well-known to those skilled in the art. However, a convenient way of acylating a compound of formula (II) with an acid of the formula $XCH_2COOH$ comprises coupling the two compounds in the presence of a carbodiimide compound. An especially convenient carbodiimide compound is 1-ethyl-3-(3-dimethylaminopropyl)carbodiimide hydrochloride, which is sometimes referred to as water-soluble carbodiimide, or WSC. This reaction is carried out by contacting substantially equivalent amounts of the acid and amine with a small excess of the carbodiimide in an appropriate solvent at a temperature in the range from $-30°$ to $100°$ C., usually from $0°$ to $30°$ C. Appropriate solvents are inactive aromatic hydrocarbons, ethers, halogenated hydrocarbons, especially dichloromethane. The reaction takes 30 minutes to 24 hours, usually 30 minutes to 3 hours at room temperature. The product can be isolated and purified by standard techniques.

The protecting group P, and any protecting group in $R^1$, $R^2$ and $R^3$ is removed by the appropriate method for the particular protecting group chosen. Thus, a typical protecting group is benzyl. This can be removed by catalytic hydrogenation. Appropriate catalysts for hydrogenation are Pd/C, Pearlman's catalyst, Pd black, or $Pd/BaSO_4$, especially 10% Pd/C.

A further convenient protecting group is the tetrahydropyranyl group (THP). This can be removed by acid-catalysed hydrolysis. Appropriate acid catalysts are organic acid, inorganic acid, or Lewis acid such as AcOH (Ac: acetyl), p-TsOH (Ts: p-toluenesulfonyl), HCl, MeAlCl (Me: metyl) etc., especially HCl.

The κ agonist compounds of formula (I), wherein $R^3$ is a $C_{1-4}$ alkyl group, can be prepared by alkylation of the corresponding compounds of formula (I), wherein R is hydroxy. This alkylation can be carried out by standard methods. A paticularly convenient method involves base catalyzed alkylation using alkyl halide in the presence of phase transfer catalyst such as tetra-n-buthylammonium hydrogen sulfate.

The intermediate hydroxylamine of Lee formula (II) can be prepared as shown in the following Scheme (II).

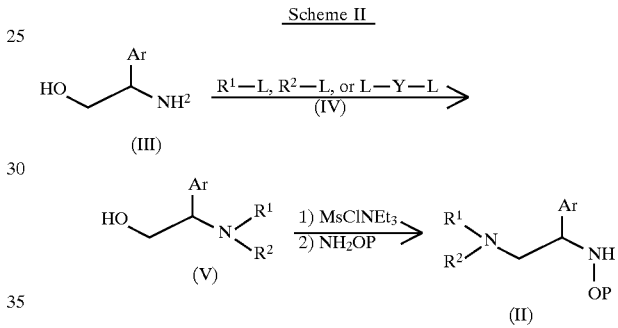

The intermediate hydroxylamine of the formula (II) can be prepared from the alcohol (V), by treatment with methanesulfonyl chloride in the presence of triethylamine followed by addition of a protected hydroxylamine ($NH_2OP$). This reaction is carried out in an appropriate solvent at a temperature in the range from $-30°$ to $100°$ C., usually from $0°$ to $30°$ C. Appropriate solvents are inactive aromatic hydrocarbons, ethers, halogenated hydrocarbons, especially dichloromethane. The reaction takes 30 minutes to 24 hours, usually 30 minutes to 3 hours at room temperature. The product can be isolated and purified by standard techniques. When an acylic amine compound as a final compound is required, the alcohol (V) is obtained from a reaction of an appropriate ethanolamine compound (III) and appropriate compound of $R^1$-L and $R^2$-L wherein L is a leaving group. When a heterocyclic compound as a final compound is required, the alcohol (V) is reacted with as compound of the formula; L—Y—L wherein Y is an appropriate bridge member. For examples, when a pyrrolino compound is prepared, —Y— is 2-butenylene. When a 2-azethidynyl is prepared, —Y— is propylene. When a 2-hexametheneimino is prepared, —Y— is hexalene.

Examples of the leaving group L are halogen, OTs or OMs(Ms: methylsulfonyl). This coupling reaction is conveniently performed preferably in the presence of a suitable base in a suitable inert solvent or diluent, for example N, N-dimethylformamide, N, N-dimethylacetamide, N-methylpyrrolidin-2-one, dimethylsulphoxide, acetone, 1, 2-dimethoxyethane or tetrahydrofuran, and at a temerature in the range of, for example, $10°$ to $150°$ C., usually $20°$ to $100°$ C.

The compounds of formula (III) and (IV) are either known compounds, which can be made by the known methods, or they are analogs of known compounds, which can be prepared by methods analogous to the known methods.

As the hydroxamic acid compounds of this invention may possess asymmetric centers, they are capable of occurring in various stereoisomeric forms or configurations. Hence, the compounds may exist in separated (+)- and (−)-optically active forms, as well as mixtures thereof. The present invention includes all such forms within its scope. Individual isomers can be obtained by known methods, such as optically selective reaction or chromatographic separation in the preparation of the final product or its intermediate.

The compounds of formula (I) of this invention are basic, and therefore they will form acid-addition salts. All such salts are within the scope of this invention. However, it is necessary to use an acid addition salts which is pharmaceutically-acceptable for administration to a mammal. The acid-addition salts can be prepared by standard methods, e.g., by contacting the basic and acidic compounds in substantially equivalent proportions in water or an organic solvent such as methanol or ethanol, or a mixture thereof. The salts can be isolated by evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of formula (I) of this invention are basic, and they will form acid salts. All such salts are within the scope of this invention. However, it is necessary to use a acid salt which is pharmaceutically-acceptable for administration to a mammal. The acid salts can be prepared by standard methods, e.g., by contacting the acidic and basic compounds in substantially equivalent proportions in water or an organic solvent such as methanol or ethanol, or a mixture thereof. The salts can be isolated by evaporation of the solvent. Typical acid salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, p-toluenesulfonate, oxalate and pamoate (1,1'-methylene-bis-(2-hydroxy-3-naphtoate)) salts.

Also included within the scope of this invention are bioprecursors (also called pro-drugs) of the κ agonist compounds of the formula (I). A bioprecursor of a κ agonist of formula (I) is a chemical derivative thereof which is readily converted back into the parent compound of formula (I) in biological systems. In particular, a bioprecursor of a κ agonist of formula (I) is converted back to the parent compound of formula (I) after the bioprecursor has been administered to, and absorbed by, a mammalian subject, e.g., a human subject. For example, it is possible to make a bioprecursor of a κ agonist of the invention of formula (I) in which OR is hydroxy groups by making an ester of the hydroxy group. When only one of A and OR is a hydroxy group, only mono-esters are possible. When OR are hydroxy, mono- and di-esters (which can be the same or different) can be made. Typical esters are simple alkanoate esters, such as acetate, propionate, butyrate, etc. In addition, when A or OR is a hydroxy group, bioprecursors can be made by converting the hydroxy group to an acyloxymethyl derivative (e.g., a pivaloyloxymethyl derivative) by reaction with an acyloxymethyl halide (e. g., pivaloyloxymethyl chloride).

The κ agonists compounds of the present invention of formula (I) exhibit significant agonist activity toward opioid κ receptor and are thus useful as analgesic, antiinflammatory, diuretic, anesthetic and neuroprotective agents, or an agent for treatment of functional bowel disease such as abdominal pain, for the treatment of mammals, especially humans in need of such agents.

The activity of the κ agonists compounds of formula (I) of the present invention, is demonstrated by the opioid receptor binding activity. Such activity may be determined in homogenates from guinea pig whole brain, as described by Regina, A. et al. in J. Receptor Res. 12: 171–180, 1992. In summary, tissue homogenate is incubated at 25° C. for 30 min in the presence of labelled ligand and test compounds. The $\mu$-sites are labelled by 1 nM of (3H)-[D-Ala2,MePhe4, Gly-ol5]enkephalin (DAMGO), the δ-sites by 1 nM of (3H)-[D-Pen2,5]enkephalin (DPDPE) and the κ-sites by 0.5 nM (3H)-CI-977. The non specific binding is measured by use of 1 mM CI-977 (κ), 1 nM (DAMGO) ($\mu$), 1 mM (DPDPE) (δ). Data are expressed as the $IC_{50}$ values obtained by a non-linear fitting program using the Cheng and Prusoff equation. All compounds of examples 1to 10 were tested by the above method, and indicated good κ-agonist activity. In this testing, all the compounds tested indicated low $IC_{50}$ values, in the range of 0.01 to 100 nM.

The activity of the κ agonists compounds can also be demonstrated by the Formalin Test as described by Wheeler-Aceto, H. et al. in Psychopharmacology 104: 35–44, 1991. In this testing, male SD rats (80–100 g) are injected s.c. with a test compound dissolved in 0.1% methyl cellulose saline or vehicle. After 30 min., 50 ml of a 2% formalin are injected into a hind paw. The number of licking the injected paw per observation period is measured 15–30 min. after the injection of formalin and expressed as % inhibition compared to the respective vehicle group.

The activity of the κ agonists can also be demonstrated by the Rotarod Test as described by Hayes, A. G. et al. in Br. J. Pharmacol. 79: 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value, defined as the dose of the drug which halves the performance time is observed in the control group.

The κ agonists compounds of formula (I) of this invention can be administered via either the oral, parenteral or topical routes to mammals. In general, these compounds are most desirably administered to humans in doses ranging from 0.01 mg to 50 mg per day, although variations will necessarily occur depending upon the weight and condition of the subject being treated, the disease state being treated and the particular route of administration chosen. However, a dosage level that is in the range of from 0.01 mg to 1 mg per kg of body weight per day, single or divided dosage is most desirably employed in humans for the treatment of pain in a postoperative patient.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparations. However, it should be understood that the invention is not limited to the specific details of these examples and preparations. Melting points were taken with a Buchi micro melting point apparatus and uncorrected. Infrared Ray absorption spectra (IR) were measured by a Shimazu infrared spectrometer (IR-470). $^1$H and $^{13}$C nuclear magnetic resonance spectra (NMR) were measured in CDCl$_3$ by a JEOL NMR spectrometer (JNM-GX270, 270 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

PREPARATION 1

(R)-2-Piperidino-2-phenylethanol

A suspension mixture of (R)-(−)-2-phenylglycinol(686 mg, 5 mmol), 1,5-dibromopentane (0.82 ml, 6 mmol), and K$_2$CO$_3$ (1.38 g, 10 mmol) in ethanol (15 ml) was refluxed with stirring for 23 h. After cooling down to rt, the white solid was removed by filtration and the filtrate was concentrated to give white solid oil mixture. This was suspended in CH$_2$Cl$_2$ (30 ml), washed with water and saturated NaHCO$_3$ aqueous solution, dried (Na$_2$SO$_4$), and concentrated to give 1.42 g of clear yellow oil. This was purified by column chromatography (silica gel: 50 g, CH$_2$Cl$_1$/MeOH:30/1 to 20/1) to afford 955 mg (93%) of desired compound as clear light yellow oil.

$^1$H NMR (270 MHz, CDCl$_3$) δ 7.38–7.29 (3H, m), 7.19–7.15 (2H, m), 3.98 (1H, t, J=9.5Hz), 3.68 (1H, dd, J=5.1, 9.2 Hz), 3.61 (1H, dd, J=5.1, 9.1 Hz), 3.30–1.70 (1H, almost flat br.s), 2.65–2.45 (2H, m), 2.35–2.15 (2H, m), 1.70–1.45 (4H, m), 1.45–1.30 (2H, m).

IR(neat): 3400 cm$^{-1}$.

EXAMPLE 1

2-(3,4-Dichlorophenyl)-N-(1-(S)-phenyl-2-piperidinoethyl)-N-tetrahydropyranyloxyacetamide To a stirred solution of (R)-2-piperidino-2-phenylethanol (0.94 g, 4.6 mmol) and triethylamine(0.77 ml, 5.5 mmol) in CH$_2$Cl$_2$(15 ml) was added methanesulfonyl chloride (0.43 ml, 5.5 mmol) dropwise at 0° C. (ice bath). After 16 h stirring at 0° C. to room temperature, the reaction mixture was washed with saturated NaHCO$_3$ aqueous solution and brine, dried(Na$_2$SO$_4$), and concentrated to give 1.074 g of brown solid and brown viscous oil mixture. This crude chloride was used for next reaction without purification.

$^1$H NMR (270 MHz, CDCl$_3$) δ 7.41–7.25 (5H, m), 4.97 (1H, dd, J=5.9, 8.1 Hz), 2.99 (1H, dd, J=8.1, 13.6 Hz), 2.78 (1H, dd, J=5.9, 13.6 Hz), 2.50–2.40 (4H, m), 1.60–1.48 (4H, m), 1.48–1.35 (2H, m).

To this mixture (1.06 g, 4.6 mmol) was added O-(tetrahydrpyranyl)hydroxylamine (832 mg, 7.11 mmol) and ethanol (10 ml) and the mixture was refluxed with stirring for 0.5 h. After evaporation of the solvent, the residue was dissolved in CH$_2$Cl$_2$(20 ml), washed with saturated NaHCO$_3$ aqueous solution and brine, dried (Na$_2$SO$_4$), and concentrated to give 1.57 g of yellow oil. This crude amine was used for next reaction without purification.

$^1$H NMR (270 MHz, CDCl$_3$) δ 7.45–7.25 (5H, m), 6.75 (0.5H, br,s), 5.48 (0.5H, br.s), 4.75–4.70 (1H, m), 4.22 (0.5H, dd, J=3.3, 11.7 Hz), 4.14 (0.5H, dd, J=4.0, 10.3 Hz), 4.00–3.87 (1H, m), 3.65–3.40 (1H, m), 2.70 (0.5H, dd, J=10.6, 12.8 Hz), 2.70–2.45 (2.5H, m, including 0.5H, dd, J=12.1, 12.8 Hz at 2.52 ppm), 2.40–2.20 (3H, m, including 0.5H, dd, J=4.0, 12.8 Hz at 2.35 ppm and 0.5H, dd, J=3.3, 13.2 Hz at 2.24 ppm), 1.95–1.15 (12H, m).

To a stirred solution of crude amine (1.5 g, 4.6 mmol) and 3,4-dichlorophenylacetic acid (1.26 g, 6.15 mmol) in CH$_2$Cl$_2$ (30 ml) was added 1-ethyl-3-(3-dimethylaminopropyl)carbodiimide hydrochloride (abbreviated as WSC, 1.18 g, 6.15 mmol) at room temperature. After 2.5 hr stirring, the reaction mixture was washed with water and saturated NaHCO$_3$ aqueous solution, dried (Na$_2$SO$_4$), and concentrated to give 2.85 g of brown viscous oil. This was purified by column chromatography (silica gel; 100 g, CH2C12/MeOH: 20/1) to give 2.027 g (89.7%) of clear yellow viscous oil.

$^1$H NMR (270 MHz, CDCl$_3$) δ 7.42–7.10 (7.5H, m), 6.95 (0.5H, dd, J=2.2, 8.4 Hz), 5.80–5.60 (1H, m, including 0.5H, dd, J=4.8, 11.0 Hz at 5.64 ppm), 5.35–5.25 (0.5H, m), 5.00–4.90 (0.5H, m), 4.14 (0.5H, d, J=16.5 Hz), 4.00–3.80

(2.0H, m, including 0.5H, d, J=15.8 Hz at 3.94 ppm and 1H, d, J=16.1 Hz at 3.86 ppm), 3.68–3.55 (0.5H, m), 3.50–3.35 (1H, m), 3.22 (0.5H, dd, J=11.0, 12.5 Hz), 3.11 (0.5H, dd, J=11.0, 12.8 Hz), 2.65–2.48 (3H, m, including 0.5H, dd, J=4.8, 13.2 Hz), 2.40–2.25 (2H, m), 1.95–1.15 (12H, m).

IR(neat): 1670 cm$^{-1}$.

EXAMPLE 2

2-(3,4-Dichlorophenyl)-N-hydroxy-N-(1-(S)-phenyl-2-piperidinoethyl)acetamide

A solution of 2-(3,4-dichlorophenyl)-N-(1-(S)-phenyl-2-piperidinoethyl)-N-tetrahydropyranyloxyacetamide (2.00 g, 4.07 mmol) in HCl gas containing MeOH (15 ml) was stirred at room temperature for 1 h. After evaporation of the solvent, the residue was basified with NH$_3$ aqueous solution and extracted with CH$_2$Cl$_2$ (total 30 ml). The extract combined was dried (Na$_2$SO$_4$) and concentrated to afford 1.47 g of brown oil.

$^1$H NMR (270 MHz, CDCl$_3$) δ 7.45 (1H, d, J=1.8 Hz), 7.41–7.24 (6H, m), 7.17 (1H, dd, J=1.8, 8.1 Hz), 5.61 (1H, dd, J=6.2, 11.0 Hz), 4.0–3.0 (1H, almost flat br.s), 3.88 (1H, d, J=14.3 Hz), 3.73 (1H, d, J=13.9 Hz), 2.99 (1H, dd, J=11.0, 12.8 Hz), 2.69 (1H, dd, J=6.2, 12.8 Hz), 2.60–2.30 (2H, m), 1.65–1.30 (8H, m).

IR(neat): 3150, 1650 cm$^{-1}$.

This oil was treated with HCl gas containing MeOH (10 ml) at rt. Then the solvent was evaporated. The residue was solved in CH$_2$Cl$_2$ and ether was added to give crystalline, which was collected by filtration to afford 1.087 g of white powder after dry in vacuo.

MS m/z: 406(M+).

mp 186.2°–188.3° C.

Anal. Calcd for C$_{21}$H$_{24}$Cl$_2$N$_2$O$_2$·HCl·0.6H$_2$O:C, 55.48; 5.81; N, 6.16.

Found: C, 55.37; H, 5.90; N, 6.28.

PREPARATION 2

(R)-2-(3-Pyrrolino)-2-phenylethanol

This was prepared from (R)-(−)-phenylglycinol and 1,4-dichloro-2-butene in 54% yield according to the procedure similar to that described in preparation 1.

$^1$H NMR (270 MHz, CDCl$_3$) δ 7.40–7.25 (5H, m), 5.77 (2H, s), 3.83 (2H, d, J=5.5 Hz), 3.68 (1H, t, J=5.5 Hz), 3.50 (4H, s), 2.05 (1H, br.s).

EXAMPLE 3

2-(3,4-Dichlorophenyl)-N-hydroxy-N-[1-(S)-phenyl-2-(3-pyrrolinoethyl)]acetamide

This was prepared from (R)-2-(3-pyrrolino)-2-phenylethanol in 44.2% overall yield according to a procedure similar to that described in example 1 and 2.

$^1$H NMR (270 MHz, CDCl$_3$) δ 7.50–7.25 (7H, m), 7.20–7.10 (1H, m), 5.71 (2H, s), 5.59 (1H, dd, J=5.5, 10.6 Hz), 3.87 (1H, d, J=14.3 Hz), 3.76 (1H, d, J=14.7 Hz), 3.60–3.35 (6H, m), 2.99 (1H, dd, J=5.5, 12.5 Hz).IR(neat): 1670 cm$^{-1}$.

HCl salt: mp 137.5°–140.0° C.

MS m/z: 390(M+).

Anal. Calcd for C$_{20}$H$_{20}$Cl$_2$N$_2$O$_2$·HCl·0.9H$_2$O:C, 54.11; 5.18; N, 6.31.

Found: C, 54.64; H, 5.69; N, 6.42.

PREPARATION 3

1-(S)-Phenyl-2-1,2,3,6-tetrahydropyridin-1-yl) ethanol and 2-(R)-phenyl-2-(1,2,3,6-tetrahydropyridin-1-yl)ethanol A mixture of 1,2,3,6-tetrahydropyridine (692 mg, 8.32 mmol) and (S)-(−)-styrene oxide(100 g, 8.32 mmol) in EtOH (10 ml) was refluxed with stirring for 2.5 h. After evaporation of the solvent, the residue was purified by column chromatography (silica gel: 50 g, CH$_2$Cl$_2$/MeOH:50/1 to 30/1) to give 1.54 g (91.1%) of colorless oil as 7 to 3 mixture of title compounds.

$^1$H NMR (270 MHz, CDCl$_3$) δ 7.45–7.20 (5H, m), 5.85–5.75 (0.6H, m), 5.75–5.58 (1.4H, m), 4.77 (0.7H, dd, J=4.0, 10.3 Hz), 4.01 (0.3H, dd, J=11.0, 12.5 Hz), 3.80–3.65 (0.6H, m), 3.30–2.72 (3.4H, m), 2.65–2.30 (3H, m), 2.30–2.10 (2H, m).

EXAMPLE 4

2-(3,4-Dichlorophenyl)-N-[1-(S)-phenyl-2-(1,2,3,6-tetrahydropyridin-1-yl)ethyl]-N-tetrahydropyranyloxyacetamide This was prepared from 1-(S)-phenyl-2-(1,2,3,6-tetrahydropyridin-1-yl)ethanol and 2-(R)-phenyl-2-(1,2,3,6-tetrahydropyridin-1-yl)ethanol in 77% overall yield according to a procedure similar to that described in example 1.

Crude chloride derivative:

$^1$H NMR (270 MHz, CDCl$_3$) δ 7.45–7.25 (5H, m), 5.77–5.68 (1H, m), 5.64–5.58 (1H, m), 5.01 (1H, dd, J=5.9, 8.1 Hz), 3.15–3.03 (3H, m, including 1H, dd, J=8.1, 13.6 Hz at 3.10 ppm), 2.92 (1H, dd, J=5.9, 13.6 Hz), 2.66 (1H, dd, J=5.5, 11.4 Hz), 2.56 (1H, dd, J=5.5, 11.4 Hz), 2.20–2.00 (2H, m).

Title compound:

$^1$H NMR (270 MHz, CDCl$_3$) d 7.45–7.20 (7H, m), 7.12 (0.5H, dd, J=1.8, 8.1 Hz), 6.97 (0.5H, dd, J=1.8, 8.1 Hz), 5.85–5.60 (3.5H, m), 5.18 (0.5H, app.d, J=4.8 Hz), 4.00–3.80 (3H, m, including 0.5H, d, J=15.8 Hz at 3.92 ppm and 0.5H, d, J=15.8 Hz at 3.83 ppm), 3.41–2.35 (7H, m), 2.18–2.08 (1H, m), 2.08–1.95 (1H, m), 1.95–1.10 (6H, m).

IR(KBr): 1685 cm$^{-1}$.

EXAMPLE 5

2-(3,4-Dichlorophenyl)-N-hydroxy-N-[1-(S)-phenyl-2-(1,2,3,6-tetrahydropyridin-1-yl)ethyl]acetamide This was prepared from 2-(3,4-dichlorophenyl)-N-[1-(S)-phenyl-2-(1,2,3,6-tetrahydropyridin-1-yl)ethyl]-N-tetrahydropyranyloxyacetamide in 100% yield according to a procedure similar to that described in example 2.

$^1$H NMR (270 MHz, CDCl$_3$) δ 7.41 (1H, d, J=2.2 Hz), 7.40–7.25 (6H, m), 7.15 (1H, dd, J=2.2, 8.4 Hz), 5.75–5.60 (2H, m), 5.51 (1H, app.br.d, J=9.9 Hz), 3.88 (1H, d, J=13.9 Hz), 3.70 (1H, d, J=13.9 Hz), 3.10 (1H, dd, J=11.4, 12.5 Hz), 2.97 (2H, d, J=2.6 Hz), 2.80 (1H, dd, J=5.9, 12.5 Hz), 2.70–2.50 (3H, m), 2.20–1.85 (2H, m).

IR(neat): 3200, 1650 cm$^{-1}$.

HCl salt: mp 191°–192.5° C.

Anal. Calcd for C$_{21}$H$_{22}$Cl$_2$N$_2$O$_2$·HCl:C, 57.09; H, 5.25; N, 6.34.

Found: C, 56.97; H, 5.23; N, 6.32.

EXAMPLE 6

2-(3,4-Dichlorophenyl)-N-(2-N,N-dimethylamino-1-(S)-phenylethyl)-N-hydroxyacetamide This was prepared from dimethylamine and (S)-(−)-styrene oxide in 18.9% overall yield according to a procedure similar to that described in preparation 3, example 4 and 5.

¹H NMR (270 MHz, CDCl₃) δ 7.42–7.25 (7H, m), 7.13 (1H. dd, J=1.8, 8.1 Hz), 5.57 (1H, dd, J=5.9, 11.4 Hz), 3.86 (1H, d, J=14.7 Hz), 3.75 (1H, d, J=14.7 Hz), 3.71 (1H, s), 3.06 (1H, dd, J=11.7, 12.1 Hz), 2.56 (1H, dd, J=5.9, 12.5 Hz), 2.25 (6H, s).

IR(neat): 3150, 1650 cm⁻¹.

HCl salt: mp 153°–157° C.

MS m/z: 366(M +)

Anal. Calcd for C₁₈H₂₀Cl₂N₂O₂·HCl ·0.3H₂O:C, 52.84; H, 5.32; N, 6.85.

Found: C, 53.21; H, 5.72; N, 7.10.

EXAMPLE 7

N-(2-Azetidinyl-1-(S)-phenylethyl)-N-hydroxy-2-(3,4-dichlorophenyl)acetamide

This was prepared from azetidine and (S)-(–)-styrene oxide in 42.5% overall yield according to a procedure similar to that described in preparation 3, example 4 and 5.

¹H NMR (270 MHz, CDCl₃) δ 7.44–7.10 (8H, m), 5.51 (1H, dd, J=5.5, 9.2 Hz), 3.90–3.10 (1H, almost flat br.s), 3.87 (1H, d, J=14.3 Hz), 3.76 (1H, d, J=14.3 Hz), 3.31–3.10 (5H, m), 2.81 (1H, dd, J=5.5, 12.5 Hz), 2.10–1.96 (2H, m).

IR(neat): 3150, 1650 cm⁻¹.

HCl salt: amorphous solid

Anal. Calcd for C₁₉H₂₀Cl₂N₂O₂·HCl·0.6H₂O:C, 51.33; H, 5.49; N, 6.30.

Found: C, 51.77; H, 5.44; N, 5.82.

EXAMPLE 8

2-(3,4-Dichlorophenyl)-N-(2-hexamethyleneimino-1-(S)-phenylethyl)-N-hydroxyacetamide This was prepared from hexamethyleneimine and (S)-(–)-styrene oxide in 26.3% overall yield according to a procedure similar to that described in preparation 3, example 4 and 5.

¹H NMR (270 MHz, CDCl₃) δ 7.45–7.10 (8H, m), 5.53 (1H, dd, J=6.6, 10.6 Hz), 3.86 (1H, d, J=13.9 Hz), 3.73 (1H, d, J=13.6 Hz), 3.05–2.89 (2H, m), 2.80–2.55 (5H, m), 1.70–1.35 (8H, m).

IR(neat): 3150, 1650 cm⁻¹.

HCl salt: mp 165°–168° C.

MS m/z: 420(M+)

Anal. Calcd for C₂₂H₂₆Cl₂N₂O₂·HCl·0.7H₂O:C, 56.17; H, 6.08; N, 5.95.

Found: C, 55.90; H, 5.94; N, 6.24.

EXAMPLE 9

2-(2,3-Dichlorophenyl)-N-hydroxy-N-[1-(S)-phenyl-2-(1,2,3,6-tetrahydropyridin-1-yl)ethyl]acetamide This was prepared from 1,2,3,6-tetrahydropyridine and (S)-(–)-styrene oxide in 47.5% overall yield according to a procedure similar to that described in preparation 3, example 4 and 5.

¹H NMR (270 MHz, CDCl₃) δ 7.45–7.24 (6H, m), 7.20–7.07 (2H, m), 5.80–5.60 (3H, m), 4.18 (1H, d, J=16.1 Hz), 3.88 (1H, d, J=16.1 Hz), 3.25–3.00 (3H, m), 2.90–2.73 (2H, m, including 1H, dd, J=5.9, 12.5 Hz at 2.83 ppm), 2.70–2.60 (1H, m), 2.30–2.10 (2H, m).

IR(KBr): 3450, 1610 cm⁻¹.

HCl salt: mp 197°–199° C.

MS m/z: 404(M+)

Anal. Calcd for C₂₁H₂₂Cl₂N₂O₂·HCl:C, 57.09; H, 5.25; N, 6.34.

Found: C, 56.95; H, 5.213; N, 6.33.

EXAMPLE 10

N-Hydroxy-N-[1-(S)-phenyl-2-(1,2,3,6-tetrahydropyridin-1-yl)ethyl]-2-(2,3,6-trichlorophenyl)acetamide This was prepared from 1,2,3,6-tetrahydropyridine and (S)-(–)-styrene oxide in 50.3 % overall yield according to a procedure similar to that described in preparation 3, example 4 and 5.

¹H NMR (270 MHz, CDCl₃) δ 7.45–7.20 (7H, m), 5.85–5.65 (3H, m), 4.33 (1H, d, J=17.3 Hz), 4.26 (1H, d, J=17.2 Hz), 3.30–3.05 (3H, m), 2.91–2.80 (2H, m, including 1H, dd, J=6.2, 12.8 Hz at 2.87 ppm), 2.75–2.65 (1H, m), 2.30–2.20 (2H, m).

IR(neat): 3300, 1650 cm⁻¹.

HCl salt: mp 189°–192° C.

MS m/z: 438(M+)

Anal. Calcd for C₂₁H₂₂Cl₂N₂O₂·HCl:C, 52.96; H, 4.66; N, 5.88.

Found: C, 52.95; H, 4.50; N, 5.90.

In addition, the chemical structure of the compounds prepared in the examples are summerized in the following Table.

TABLE

Structure (I): R¹R²N–CH₂–CH(Ar)–N(OR³)–C(O)–CH₂–X

| Example # | R¹R²N– | R³ | X– |
|---|---|---|---|
| 1 | piperidin-1-yl | THP | 3,4-dichlorophenyl |
| 2 | piperidin-1-yl | H | 3,4-dichlorophenyl |
| 3 | 2,5-dihydropyrrol-1-yl | H | 3,4-dichlorophenyl |
| 4 | 1,2,3,6-tetrahydropyridin-1-yl | THP | 3,4-dichlorophenyl |
| 5 | 1,2,3,6-tetrahydropyridin-1-yl | H | 3,4-dichlorophenyl |

TABLE-continued

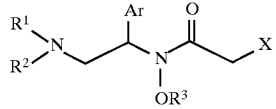

| Example # | R¹ \ N— / R² | R³ | X— |
|---|---|---|---|
| 6 | dimethylamino | H | 3,4-dichlorophenyl |
| 7 | azetidinyl | H | 3,4-dichlorophenyl |
| 8 | hexamethyleneimino | H | 3,4-dichlorophenyl |
| 9 | 1,2,3,6-tetrahydropyridin-1-yl | H | 2,3-dichlorophenyl |
| 10 | 1,2,3,6-tetrahydropyridin-1-yl | H | 2,3-dichloro-6-ethylphenyl |

I claim:

1. A compound of the following formula:

$$\underset{R^2}{\overset{R^1}{\diagdown}}N\diagdown\underset{\underset{OR^3}{|}}{\overset{Ar}{\diagup}}\diagdown N\diagdown\underset{O}{\overset{\|}{C}}\diagdown X \quad (I)$$

and its pharmaceutically acceptable salt thereof, wherein $R^1$ and $R^2$ are independently hydrogen, $C_{1-4}$ alkyl, $C_{3-7}$ cycloalkyl, $C_{2-4}$ alkenyl, $C_{1-4}$ alkoxy, $C_{1-4}$ alkylthio, phenyl or phenyl-$C_{1-4}$alkyl; or $R^1$ and $R^2$ are taken together with the nitrogen to which they are attached and form an optionally substituted, saturated or unsaturated 3-, 4-, 5-, 6- or 7-membered mono-heterocyclic ring system optionally containing an additional heteroatom selected from nitrogen, oxygen or sulfur, provided that the heterocyclic is not pyrrolidinyl;

$R^3$ is hydrogen, $C_{1-4}$ alkyl or a hydroxy protecting group;

Ar is phenyl optionally substituted with one or more substituents selected from halo, hydroxy, $C_{1-4}$ alkyl, $C_{1-4}$ alkoxy, $C_{1-4}$ alkoxy-$C_{1-4}$ alkyloxy, $CF_3$ and carboxy-$C_{1-4}$ alkyloxy; and X is phenyl, naphthyl, biphenyl, indanyl, benzofuranyl, benzothiophenyl, 1-tetralone-6-yl, $C_{1-4}$ alkylenedioxy, pyridyl, furyl or thienyl, these groups being optionally substituted with up to three substituents selected from halo, $C_{1-4}$ alkyl, $C_{1-4}$ alkoxy, hydroxy, $NO_2$ $CF_3$ and $SO_2CH_3$.

2. A compound according to claim 1, wherein $R^1$ and $R^2$ taken together forms a 5- or 6-membered cyclic amino group optionally substituted with one to three substituents selected from hydroxy, halo, $C_{1-4}$ alkyl and —OY wherein Y is a hydroxy protecting group.

3. A compound according to claim 2, wherein Ar is phenyl.

4. A compound according to claim 3, wherein X is phenyl substituted with up to three substituents selected from chloro, methyl and $CF_3$; and $R^3$ is hydrogen.

5. A compound according to claim 4, wherein X is 3,4-dichlorophenyl.

6. A compound according to claim 1, being one of the following:
2-(3,4-dichlorophenyl)-N-(1-(S)-phenyl-2-piperidinoethyl)-N-tetrahydropyranyloxyacetamide;
2-(3,4-dichlorophenyl)-N-hydroxy-N-(1-(S)-phenyl-2-piperidinoethyl)acetamide;
2-(3,4-dichlorophenyl)-N-hydroxy-N-[1-(S)-phenyl-2-(3-pyrrolinoethyl)]acetamide;
2-(3,4-dichlorophenyl)-N-[1-(S)-phenyl-2-(1,2,3,6-tetrahydropyridin-1-yl)ethyl]-N-tetrahydropyranyloxyacetamide;
2-(3,4-dichlorophenyl)-N-hydroxy-N-[1-(S)-phenyl-2-(1,2,3,6-tetrahydropyridin-1-yl)ethyl]acetamide;
2-(3,4-dichlorophenyl)-N-(2-N,N-dimethylamino-1-(S)-phenylethyl)-N-hydroxyacetamide;
N-(2-azetidinyl-1-(S)-phenylethyl)-N-hydroxy-2-(3,4-dichlorophenyl)acetamide;
2-(3,4-dichlorophenyl)-N-(2-hexamethyleneimino-1-(S)-phenylethyl)-N-hydroxyacetamide;
2-(2,3-dichlorophenyl)-N-hydroxy-N-[1-(S)-phenyl-2-(1,2,3,6-tetrahydropyridin-1-yl)ethyl]acetamide; and
N-hydroxy-N-[1-(S)-phenyl-2-(1,2,3,6-tetrahydropyridin-1-yl)ethyl]-2-(2,3,6-trichlorophenyl)acetamide.

7. A compound according to claim 1, being one of the following:
2-(3,4-dichlorophenyl)-N-hydroxy-N-(1-(S)-phenyl-2-piperidinoethyl)acetamide;
2-(3,4-dichlorophenyl)-N-hydroxy-N-[1-(S)-phenyl-2-(3-pyrrolinoethyl)]acetamide; and
2-(3,4-dichlorophenyl)-N-hydroxy-N-[1-(S)-phenyl-2-(1,2,3,6-tetrahydropyridin-1-yl)ethyl]acetamide.

8. A pharmaceutical composition useful for treating pain, inflammation or functional bowel disease or for eliciting antitussive, diuretic or anesthetic activity in a mammal in need of such treatment, said composition comprising a therapeutically-effective amount of a compound according to claim 1 and a pharmaceutically acceptable carrier.

9. A method for treating pain, inflammation or functional bowel disease, or for eliciting antitussive, diuretic or anesthetic activity in a mammal in need of such treatment, which comprises administering to said mammal a therapeutically-effective amount of a compound according to claim 1.

* * * * *